United States Patent [19]

Michaels et al.

[11] Patent Number: 5,342,298
[45] Date of Patent: Aug. 30, 1994

[54] AUTOMATED FLUID PRESSURE CONTROL SYSTEM

[75] Inventors: Mary B. Michaels, Sunnyvale; Janine C. Robinson, Half Moon Bay; John P. Claude, San Carlos; Donald L. Alden, Sunnyvale, all of Calif.

[73] Assignee: Advanced Cardiovascular Systems, Inc., Santa Clara, Calif.

[21] Appl. No.: 923,063

[22] Filed: Jul. 31, 1992

[51] Int. Cl.⁵ .............................................. A61M 1/00
[52] U.S. Cl. ......................................... 604/65; 604/97; 604/143; 128/DIG. 1; 128/DIG. 12
[58] Field of Search ............... 604/30, 65, 67, 97, 604/98, 141, 143, 147, 151, 154, 146, 96; 128/DIG. 1, DIG. 12

[56] References Cited

U.S. PATENT DOCUMENTS

| | | | |
|---|---|---|---|
| 2,865,371 | 12/1958 | Dorbecker et al. | 604/143 |
| 3,701,345 | 10/1972 | Heilman et al. | 604/67 |
| 3,720,199 | 3/1973 | Rishton et al. | |
| 4,446,867 | 5/1984 | Leveen et al. | |
| 4,651,738 | 3/1987 | Demer et al. | |
| 4,743,230 | 5/1988 | Nordquest et al. | 604/97 |
| 4,758,223 | 7/1988 | Rydell | 604/98 |
| 4,781,192 | 11/1988 | Demer | |
| 4,795,424 | 1/1989 | Burner | 604/30 |
| 4,841,977 | 6/1989 | Griffith et al. | |
| 4,854,324 | 8/1989 | Hirschman et al. | 128/DIG. 1 |
| 4,872,483 | 10/1989 | Shah | 137/557 |
| 4,877,035 | 10/1989 | Bogen et al. | |
| 4,941,475 | 7/1990 | Williams et al. | |
| 4,944,726 | 7/1990 | Hilal et al. | 604/143 |
| 4,955,377 | 9/1990 | Lennox et al. | |
| 4,976,725 | 12/1990 | Chin et al. | 606/192 |
| 4,998,914 | 3/1991 | Wiest et al. | 604/67 |
| 5,015,233 | 5/1991 | McGough et al. | 604/97 |
| 5,019,041 | 5/1991 | Robinson et al. | 604/97 |
| 5,021,046 | 6/1991 | Wallace | 604/67 |
| 5,027,812 | 7/1991 | Shapiro et al. | |
| 5,066,276 | 11/1991 | Wang | 604/143 |
| 5,087,244 | 2/1992 | Wolinsky et al. | 604/53 |
| 5,135,488 | 8/1992 | Foote et al. | 604/97 |
| 5,152,776 | 10/1992 | Pinchuk | 604/97 |

FOREIGN PATENT DOCUMENTS

| | | | |
|---|---|---|---|
| 3338758 | 5/1985 | Fed. Rep. of Germany | 604/65 |
| 8600534 | 1/1986 | PCT Int'l Appl. | 604/151 |

*Primary Examiner*—Ralph Lewis
*Attorney, Agent, or Firm*—Fulwider, Patton, Lee & Utecht

[57] ABSTRACT

Providing fluid to an internal delivery site of a patient includes moving the fluid from a fluid reservoir through a conduit and through a delivery device at the delivery site while maintaining the fluid at a predetermined pressure. The delivery device may comprise an inflatable balloon with apertures formed in its periphery for directing the fluid into the vessel walls. Pressurized fluid is provided through the apertures of the balloon to the vessel wall. The pressure is automatically controlled to avoid both pressure spikes and unacceptable deflation of the balloon during administration of the fluid. A further feature includes comparing the pressure with the volume infused and in the event that pressure decreases while the volume infused increases beyond certain limits, the delivery of the fluid is stopped. Further features include a timer for limiting the inflation time of the delivery device and a volume detector for controlling the amount of fluid delivered. In one described embodiment, a pneumatic driver system is used to pressurize the fluid.

21 Claims, 6 Drawing Sheets

AUTOMATED FLUID PRESSURE CONTROL SYSTEM

BACKGROUND

The invention relates generally to fluid control and, more particularly, to automated control over fluid delivery pressure.

Infusion pumps are used to more precisely control the infusion of medical fluids into the vascular system of a patient. Syringe pumps are one type of an infusion pump in which the syringe plunger is moved into the syringe barrel at a controlled rate to administer the syringe contents to the patient. Such pumps are typically used to administer the infusion fluid generally as opposed to locally. That is, the medical fluid is placed into the bloodstream of the patient for general distribution throughout the body rather than applying the medical fluid only to a localized delivery site in the body. Consequently, such pumps are typically controlled to deliver the medical fluid in accordance with a desired flow rate rather than at a precisely controlled pressure.

While many such pumps include a pressure sensor, the sensed pressure is typically used only to trigger pressure alarms that will shut off the flow from the syringe pump if an occlusion or other undesirable condition is detected. The pressure provided by the pump is often only controlled to reside in a particular pressure range, which may be relatively wide, and to remain below a predetermined upper limit; the range and upper limit being selected in dependence upon the particular application.

However, in the case of local drug delivery systems for injecting medical fluids into the walls of blood vessels, into body organs or other internal delivery sites, pressure control is a primary fluid delivery parameter. In some cases, it is desirable to treat a disease by locally applying a medical drug in a high concentration. The concentration may be so high that the drug could cause damage to other parts of the body or even be life threatening if allowed to freely enter the blood stream of the patient, yet the drug may have the desired effect if confined to a local application. In such local applications, it has been found that pressure control is important. Excessive pressure may cause a dissection of the vessel wall and too little pressure will not force the medical fluid into the vessel wall but may allow it to be swept away by the bloodstream before it can be delivered to the desired location.

Studies have indicated that the application of particular medical fluids to the vessel walls following the performance of an angioplasty procedure on those walls has the potential of impeding restenosis at that site. For example, see Wolinsky et al., *Local Introduction Of Drugs Into The Arterial Wall: A Percutaneous Catheter Technique*, Journal of Interventional Cardiology, Vol. 2, No. 4, 1989, pgs 219–228. These studies indicate that the application pressure of the medical fluid to the vessel walls contributes greatly to the success or failure of the treatment. Thus, it would be of value to precisely control the pressure of the medical fluid applied in such a procedure.

The inflation balloons used in such catheter based, local introduction techniques typically include a certain number and size of apertures through which the medical fluid will be delivered to the vessel walls. The balloon is positioned at the desired location in the vessel and pressure is applied to inflate the balloon. However, the apertures tend to impede a rapid inflation because they allow a part of the inflation pressure to escape. Additionally, the apertures may allow some of the inflation fluid to escape into the bloodstream during inflation. In the case where the fluid to be applied to the vessel walls has some higher level of toxicity to the patient if the fluid should enter the bloodstream, a more rapid balloon inflation is desired. One means of achieving a more rapid inflation is to apply a higher pressure during initial inflation to force the balloon into its operative configuration as soon as possible and then lower the pressure to maintain the target pressure. An automated system would be desirable to achieve this control over inflation.

Additionally, while the balloon is inflated, and even when only partially inflated, the blood flow is interrupted or at least impeded. To avoid injury to the patient, a time limit on the inflation is imposed. Therefore, full inflation of the balloon should occur as rapidly as possible so that administration of the medical fluid can be started as soon as possible so that all of the medical fluid can be applied to the delivery site before expiration of the time limit.

More precise pressure control is also desired where the medical fluid applied to the vessel walls has some higher level of toxicity to the patient if the fluid should enter the bloodstream. In this case, it is necessary to maintain the balloon at a predetermined pressure throughout the application of the drug to lessen its chances of entering the bloodstream. The balloon must be kept at a high enough pressure so that the apertures formed in the balloon are in extremely close contact with the vessel walls. That is, the balloon cannot be permitted to deflate to an extent where the apertures are exposed to the bloodstream so that the medical fluid would be taken from the delivery site by the blood flow. By this means, drugs which may be somewhat toxic if applied to the patient through the bloodstream may be locally applied to the walls of a blood vessel to perform a post-angioplasty or other function while not adversely affecting the patient.

In one type of prior inflation/deflation system, a syringe is attached to the proximal end of a catheter containing the balloon and a pressure gauge is located adjacent the syringe to measure the pressure of the medical fluid in the catheter. The plunger of the syringe is manually moved into the syringe barrel to expel the fluid contents from the syringe through the catheter and into the vessel walls through the balloon apertures. The pressure indicated on the pressure gauge is monitored by the operator during the movement of the syringe plunger and the operator varies the movement of the syringe plunger in an attempt to maintain the desired pressure. It has been found that manual methods such as this typically do not adapt quickly enough to compensate for pressure variances as the fluid is being delivered into the vessel walls. Pressure variances may be caused by various factors including site geometry, blood pressure, the number of apertures in the balloon, catheter geometry, and the viscosity of the medical fluid being applied, for example.

A drop in the pressure indicated on the pressure gauge may stimulate the operator to accelerate the movement of the plunger into the syringe barrel which may result in a pressure spike. High pressures have been found to result in necrosis of the inner media of the vessel (Wolinsky et al., id.) and if too high, dissection of the vessel. Low pressures have the effect of transmitting the drug into the bloodstream, as discussed above. Thus, it is desirable to provide a system which permits a more rapid response time with more precise control over the pressure.

A further consideration in such systems is deflation and removal of the delivery device. In the case where the delivery device comprises an inflatable balloon having apertures for applying a medical fluid, deflation should occur so that the drug remaining in the balloon is captured by the catheter, rather than being released into the blood stream. Applying a pressure below the pressure of the delivery site, which in some cases may require a negative pressure, should occur relatively rapidly so that the medical fluid is not released into the bloodstream. The pressure in the system may change as the balloon is collapsed, thus monitoring the pressure and correcting it as it varies during removal of the balloon is desirable. Applying a negative pressure which is too large will unnecessarily draw blood or other body fluids into the catheter while too little negative pressure may allow the medical fluid to enter into the bloodstream.

In an angioplasty system in which a catheter having an inflatable balloon is positioned at a delivery site for applying pressure to the vessel walls by inflating the balloon, more precise pressure control may also provide a benefit. Although this is a closed system in that the inflation fluid is not continuously leaving the system as in the drug delivery system, pressure must be monitored for proper performance of the procedure. Excessive pressure may cause damage to the vessel walls while insufficient pressure will not expand the vessel walls enough to successfully accomplish the angioplasty.

It has also been found desirable in many drug delivery systems to more precisely control the volume of the medical fluid delivered along with more precise pressure control. In some applications, the volume of the drug to be applied to the delivery site, such as blood vessel walls, is very small (less than five milliliters). Present fluid injection systems have not permitted the precise control over pressure in the delivery of such a small amount of fluid.

Hence, it has been recognized by those skilled in the art that a more accurate fluid pressure control system is desirable. It has also been recognized that a system which provides automated control over pressure during the delivery of fluid is also desirable. It has been further recognized that a system which accurately controls pressure during the local application of medical fluid while avoiding infusion of the medical fluid into other areas is desirable. The present invention fulfills these needs and others.

SUMMARY OF THE INVENTION

The present invention provides for the local administration of fluid at a predetermined pressure through a delivery device positioned at a site internal to the body of a patient. Delivery is achieved by an apparatus which comprises a reservoir containing the fluid to be delivered and a conduit such as a catheter, connected between the reservoir and the delivery device. A pressure sensor senses pressure indicative of the fluid pressure and provides a sensed pressure signal representative thereof. A controller automatically receives the sensed pressure signal, automatically compares the sensed pressure to the predetermined delivery pressure and automatically provides a pressure error signal representative of the difference. A driving means automatically varies the pressure of the fluid being administered to the delivery site in response to the pressure error signal from the controller to automatically attain the predetermined pressure.

In a method for locally administering a fluid at a predetermined pressure to a patient at a site internal to the body of the patient, the fluid to be delivered is contained in a reservoir and pressure is applied to move the fluid from the reservoir through a fluid conduit and through a delivery device to the delivery site. Pressure is automatically sensed to indicate the pressure of the fluid and a sensed pressure signal representative of the sensed pressure is automatically compared to the predetermined pressure. A pressure error signal is provided in the event that the two pressures are different and the pressure of the fluid is automatically varied in accordance with the pressure error signal to attain the predetermined pressure.

In another aspect of the invention, a pneumatic driving means varies the volume of the reservoir to control the fluid pressure. In the case where the fluid reservoir comprises a syringe having a barrel containing the fluid to be administered, the barrel is coupled to the catheter and the pneumatic driving means forces the syringe plunger into the barrel to control the fluid pressure. The driving means moves the plunger more rapidly or more slowly in accordance with the error signal.

In another aspect of the invention, a volume detector is provided which detects the volume of the fluid delivered and provides a volume signal representative of the detected volume. The controller automatically compares the volume signal to the volume selected for delivery and controls the driving means to cease delivery of the fluid when the selected volume has been delivered. The volume detector may comprise a displacement detector to detect the movement of the driving means or the syringe plunger. The position of the selected movable device indicates the amount of fluid delivered. This may then be compared to the amount desired to be delivered and the driving means stopped at the time that the selected amount has been delivered. A linear resistor may be used as the displacement detector and may detect the position of the syringe plunger through a linkage attached to the driving means. The voltage from the linear resistor can be used to indicate the absolute position, including the end-of-travel position, of the driver.

Another feature involves detecting the end of travel of the driving means. In the case where a linear resistor is used to detect displacement, failure of the resistance to change over a period of time may be used to indicate end-of-travel.

In yet another feature, the controller monitors the sensed pressure signal while monitoring the volume of fluid delivered. In the case where the pressure decreases below a predetermined threshold while the volume delivered continues to increase, an alarm is provided and the delivery of fluid may be stopped.

In another aspect of the invention, the operator may select reverse movement of the driving means, so that the fluid in not delivered through the delivery device to the site but is drawn back into the catheter or syringe. This feature would allow deflation of the balloon and would prevent the delivery of the medical fluid to the bloodstream during removal of the catheter.

In a further aspect, the controller automatically times the sensed pressure signal for the amount of time the sensed pressure exceeds a predetermined pressure threshold and upon reaching a predetermined time limit, for example forty-five seconds, automatically controls the driving means to cease delivery of the fluid. In the case where a balloon is used, the driving means may also be commanded to deflate the balloon.

Other aspects and advantages of the invention will become apparent from the following detailed description and the accompanying drawings, illustrating, by way of example, the features of the invention.

DETAILED DESCRIPTION OF PREFERRED EMBODIMENTS

Figure 1:
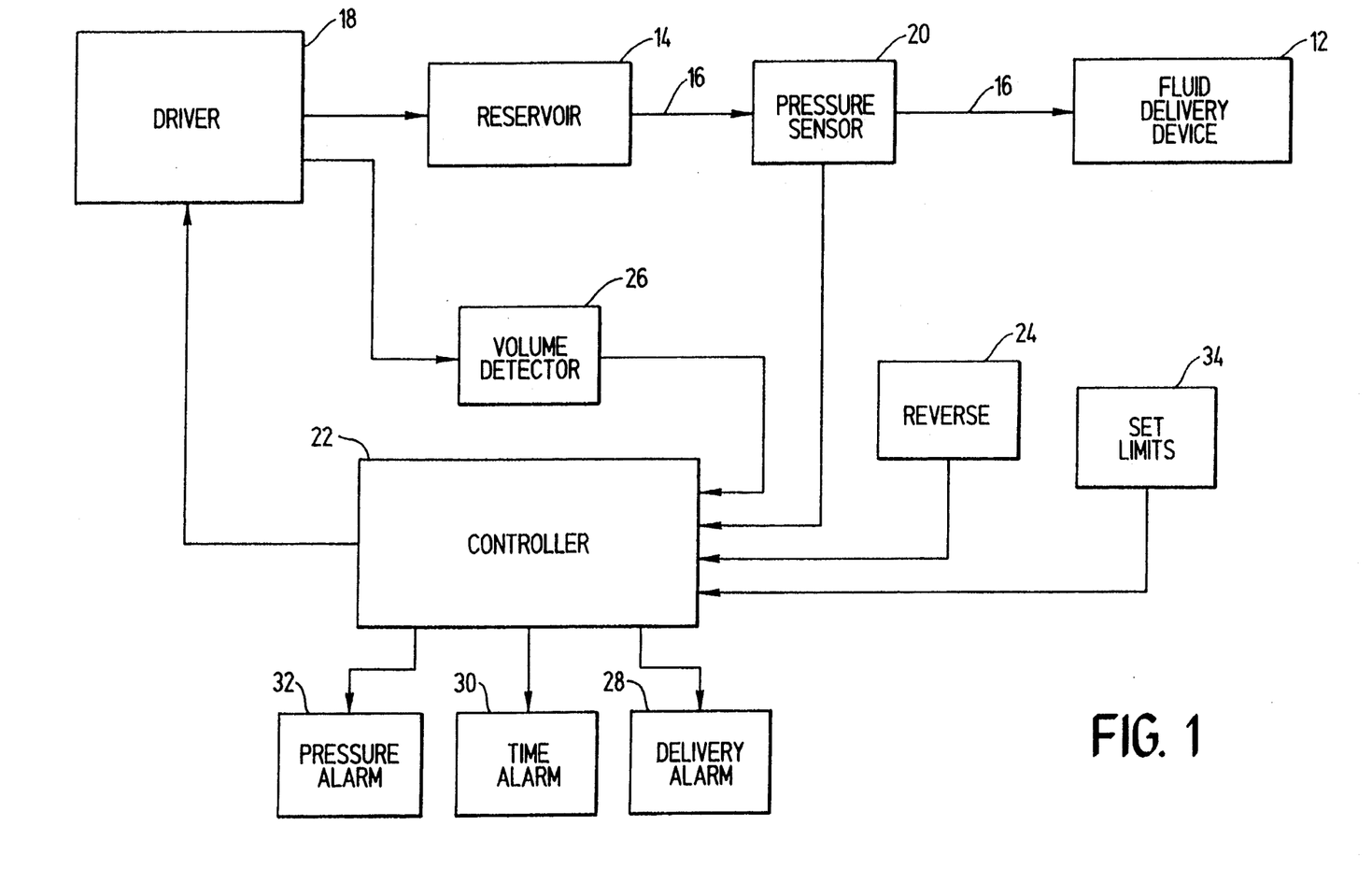
FIG. 1 is a block diagram of an automated fluid pressure control system having both pressure and volume control features.

Referring now to the drawings with more particularity, wherein like reference numerals designate like or corresponding elements among the several views, there is shown in FIG. 1 an automated fluid pressure control system 10 which provides a fluid to a fluid delivery device 12. The fluid delivery device 12 may comprise an inflatable balloon having apertures through which the supply fluid is locally administered to a delivery site internal to the body of a patient. The delivery site may comprise the walls of a blood vessel.

A reservoir 14 containing the fluid to be delivered is connected to the delivery device 12 by a conduit, such as a lumen of a catheter 16. A driver 18 provides pressure to move the fluid from the reservoir 14 through the catheter 16 to the delivery device 12. The pressure provided by the driver 18 is selected to maintain the balloon in the inflated state and force the fluid through the apertures of the balloon into the vessel walls. The pressure is maintained high enough so that the fluid leaving the balloon will only be administered to the walls of the blood vessel and will not flow to any significant extent into the bloodstream. At the same time, the pressure is not so high as to cause damage to the vessel. The size of the balloon is selected such that when inflated, some pressure will be applied by the balloon to the vessel walls to confine the apertures to intimate contact with those vessel walls. A balloon having a size too small will allow the medical fluid leaving the apertures to be swept away by the bloodstream while a balloon with a size too large may cause damage to the vessel when inflated.

A pressure sensor 20 in this embodiment senses the pressure in the conduit between the reservoir 14 and the delivery device 112 and provides a sensed pressure signal to a controller 22. The controller 22 compares the sensed pressure to a desired administration pressure and outputs an error signal in the event that they differ. The error signal is provided to the driver 18 which alters the pressure of the medical fluid to attain the desired administration pressure.

In the embodiment shown in FIG. 1, the driver 18 alters the volume of the reservoir 14 thereby controlling the pressure of the fluid in the system. Because the delivery device 12 permits the outflow of the fluid provided by the reservoir 14, the driver 18 must continually empty the reservoir 18 to maintain the desired administration pressure. In the event that the sensed pressure is less than the desired administration pressure, the rate at which the reservoir 14 is emptied by the driver 18 will be increased to raise the pressure. In the event that the sensed pressure is above the desired administration pressure, the rate at which the reservoir 14 is emptied by the driver 18 will be decreased to lower the pressure.

In another feature, the controller 22 may also receive a reverse control signal 24 from an operator in which case the controller 22 will control the driver 18 to stop the flow of the medical fluid. In the case where an inflatable balloon is used as the delivery device, the driver may reverse the flow to deflate the balloon and to assure that none of the medical fluid leaves the delivery device 12 during withdrawal from the patient. The driver 18 may accomplish this by increasing the volume of the reservoir thereby creating negative pressure.

In another aspect shown in FIG. 1, a volume detector 26 determines the amount of fluid delivered to the delivery device 12 and provides a volume signal to the controller 22. The volume signal is compared by the controller 22 to a desired volume to be administered and in the event that the two are equal, the controller 22 controls the driver 18 to cease delivery of the fluid to the delivery device 12. The volume detector 26 may take different forms, one of which is a monitor of the movement of the driver 18. Where certain positions of the driver 18 are correlated with certain volumes of fluid expelled from the reservoir 14, the amount of fluid delivered can be determined from the position of the driver 18.

Additionally, the volume detector 26 may also determine the end-of-travel position of the driver 18 and upon reaching that position, output a signal to the controller 22 which in turn may then automatically control the driver 18 to cease delivery of the fluid. An embodiment of an alternate end-of-travel arrangement is discussed in greater detail below.

In accordance with another aspect of FIG. 1, the controller 22 compares the pressure sensed by pressure sensor 20 to the volume of fluid delivered as detected by the volume detector 26. In the event that the rate of fluid delivered remains the same but the pressure sensed decreases below a predetermined minimum, for example two atmospheres, and stays them for a selected period of time, for example two seconds, the controller 22 will provide a delivery alarm 28. This delivery alarm 28 is intended to indicate a fluid delivery problem.

In accordance with another feature of the invention, the controller 22 monitors the time of the delivery of the fluid from the reservoir 14. Upon receiving from the pressure sensor 20 an indication that the desired administration pressure has been reached, the controller 22 may then begin to time the administration of the fluid to the delivery site and upon reaching the time limit, provide a time alarm 30 and/or cause the driver 18 to cease delivery. For example, where a dilatation balloon is used for applying the fluid to the walls of a blood vessel, the predetermined time limit may be set at a safe period of blood flow interruption so as not to harm the patient, for example, ninety seconds. Upon reaching that time limit, the controller 22 may automatically issue the time alarm 30 and automatically control the driver 18 to deflate the balloon.

The controller 22 may also include a maximum pressure limit. In the event that the pressure exceeds that limit, the controller 22 will provide a pressure alarm 32 and immediately lower the pressure such as by controlling the driver 18 to cease operation. For example, a pressure limit of eight atmospheres may be input to the controller 22. If the pressure of the fluid should exceed eight atmospheres, delivery would be immediately stopped and the pressure alarm 32 provided.

The desired administration pressure, pressure alarm limit and time alarm limit may be set into the controller 22 via front panel controls 34, a keyboard or other means. The front panel may also contain a switch for reverse drive 24 of the driver 18 to accomplish deflation of the delivery device 12.

Figure 2:
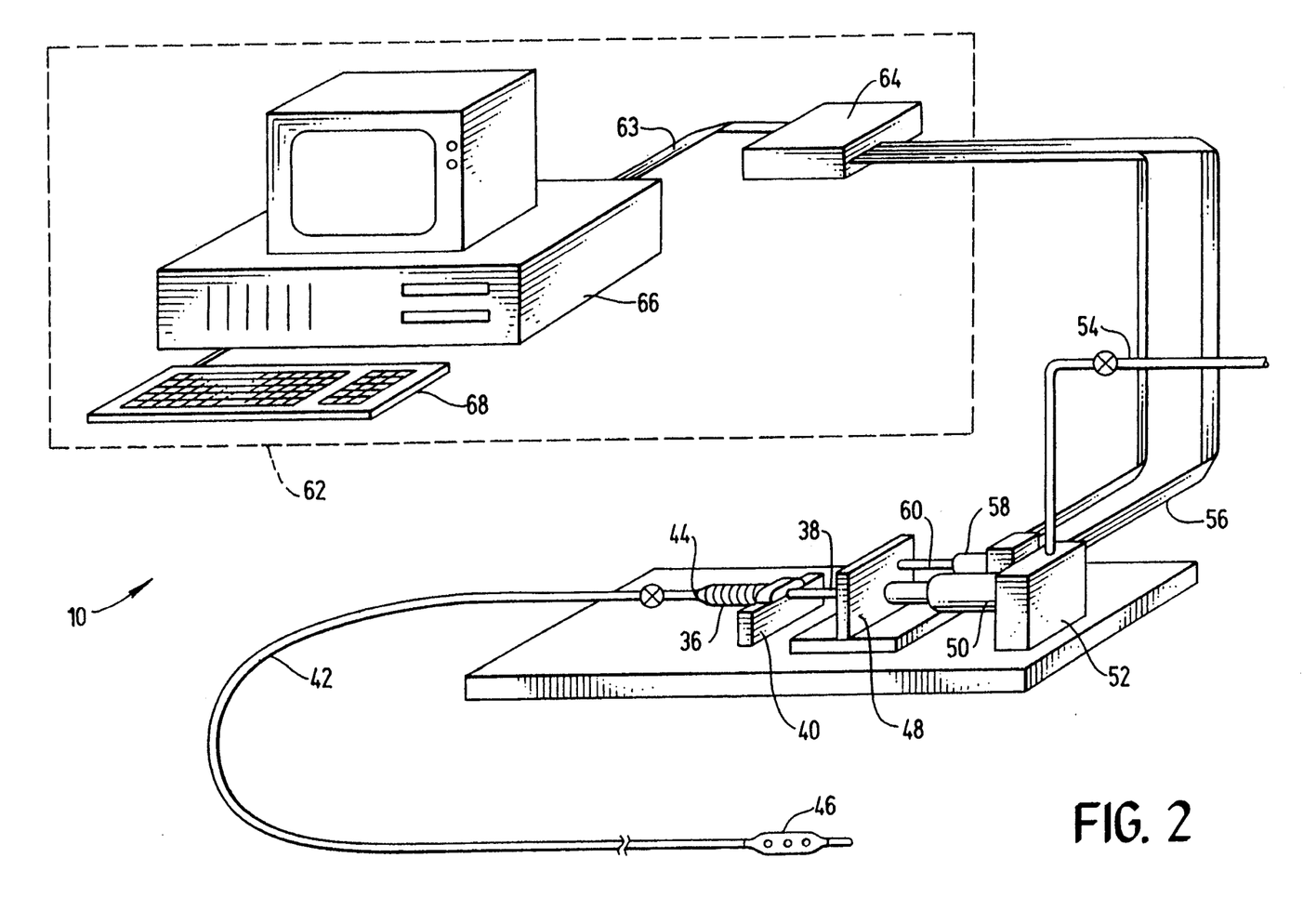
FIG. 2 is a schematic/block diagram of an automated fluid pressure control system supplying a medical fluid to an inflation balloon using a pneumatic driver, a syringe as the fluid reservoir and having a volume detector.

Referring now to FIG. 2, a more derailed drawing of an embodiment of an automated fluid pressure control system 10 in accordance with the invention is presented. In this FIGURE, the reservoir takes the form of a syringe 36 and the syringe plunger 38 operates to vary the volume of the syringe 36 by moving farther into or out of the syringe barrel. The syringe barrel is rigidly mounted by means of a mounting member 40. A dilatation catheter 42 is connected to the output port 44 of the syringe and has a dilatation balloon 46 mounted at its distal end.

The driver comprises in this case a slide mechanism 48 coupled to the syringe plunger 38 for moving the syringe plunger 38 in relation to the syringe barrel, an air cylinder 50 and an air controller 52 comprising a solenoid valve (not shown) and a control circuit (not shown). A pneumatic power source, in this case a source of air pressure, is supplied to the air controller 52 via an input line 54. The air controller 52 receives the air pressure from the air pressure line 54 and controls that air pressure in accordance with the desired administration pressure set into the air controller 52 along electrical line 56.

In one embodiment, the air controller 52 comprises an electro-pneumatic regulator having the model designation of "QB" and manufactured by Proportion-Air, Inc. of McCordsville, Ind. This particular regulator incorporates a closed loop pressure control system where the pressure output of the regulator is sensed by a pressure transducer and is compared to the pressure signal set in the electronic control circuit of the regulator. In the event that a difference is sensed between the two pressures, the internal control circuit of the regulator changes the pressure output. The output pressure from the regulator is coupled to the air cylinder 50 which applies force against the syringe plunger 38 to move it relative to the syringe barrel thereby affecting the pressure of the fluid in the syringe. Because of this direct physical link, the pressure sensed at the output of the regulator 52 is therefore indicative of the pressure of the fluid in the syringe 36.

The solenoid valve (not shown) of the air controller 52 may be switched to port the output air pressure from the regulator to one side or the other of the air cylinder to cause the syringe plunger 38 to either move farther into the syringe barrel or more farther out of the syringe barrel.

A displacement detector 58 is also shown in FIG. 2 and detects the position of the slide mechanism 48. In this case, the displacement detector 58 comprises a linear resistor having a wiping contact connected to a linkage 60 which is connected to the slide mechanism 48 for moving the syringe plunger 38. The wiping contact varies the voltage across the linear resistor 58 in dependence upon the position of the slide mechanism 48. Because the slide mechanism 48 is directly connected to the syringe plunger, the position of the slide mechanism 48 corresponds to the position of the syringe plunger 38. Thus, the amount of fluid provided from the syringe 36 can be determined by the voltage of the linear resistor 58.

The controller 62 of FIG. 2 comprises two main parts, an interface unit 64 which comprises an analog-to-digital converter (A-to-D converter) and a digital-to-analog converter (D-to-A converter), a bus 63, and a processor 66. The processor 66 in this case comprises a micro-computer but may comprise other types of processors. The output signal of the linear resistor 58 is analog in form and is provided to the interface unit 64 for conversion to a digital signal before forwarding it on to the processor 66. The desired delivery pressure of the syringe fluid is input in the processor 66 through the keyboard 68 in this case. The processor 66 provides a digital output signal representative of the pressure which is converted to an analog signal by the interface unit 64. That analog pressure signal is provided to the electro-pneumatic regulator 52 to control the air cylinder 50 and the slide mechanism 48. In this embodiment, the pressure controller would include the main controller 62 which provides the control signal for the desired pressure and also the pressure controller which is built into the QB electro-pneumatic regulator.

An A-to-D converter found usable is the DASCON-1, from Metabyte, Inc. which is a twelve-bit converter, although other converters may be used. A displacement detector which may be used is the LT-103 from Waters Manufacturing.

Figure 3:
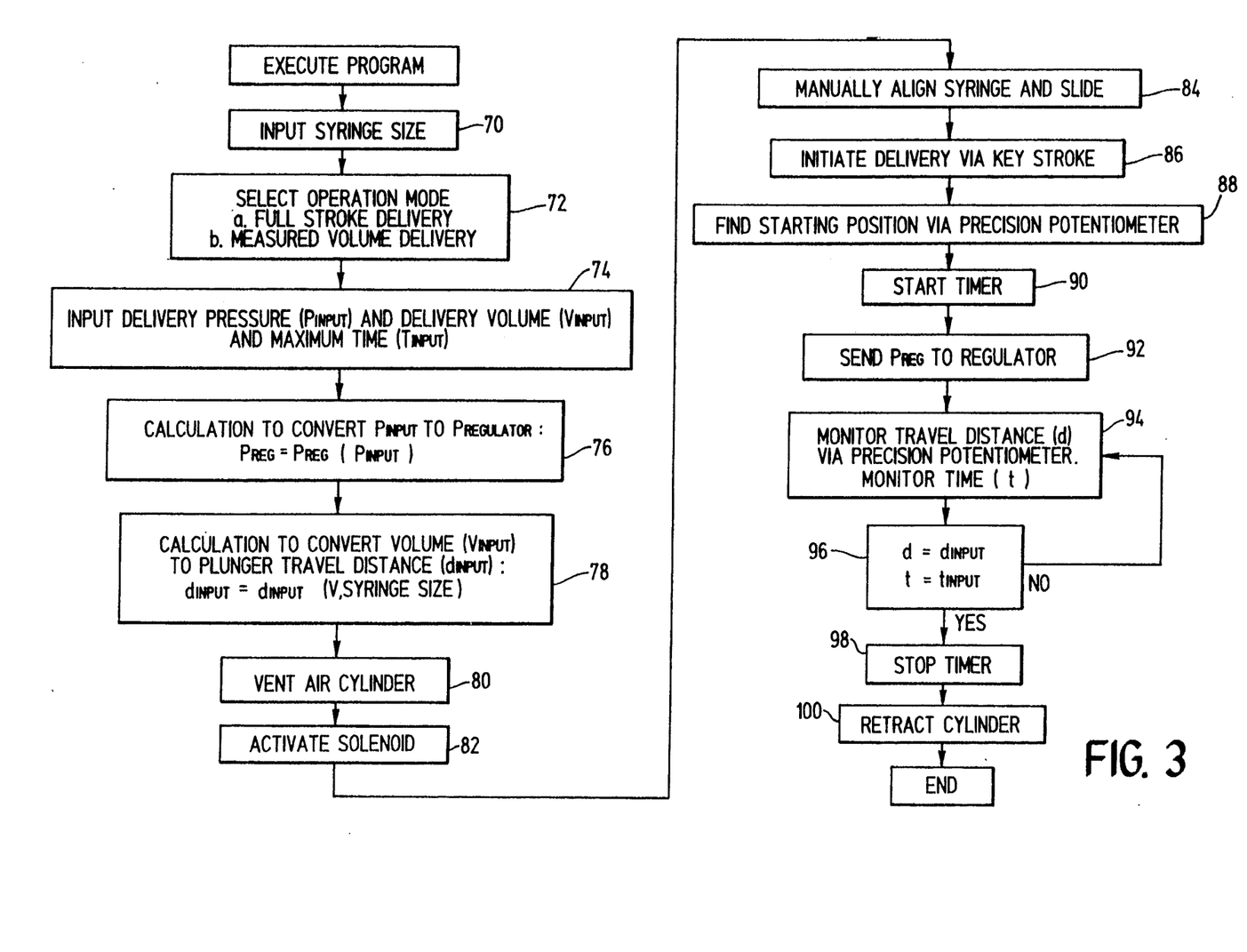
FIG. 3 is a flow chart presenting a method of automated fluid pressure control in an automated fluid pressure control system such as that shown in FIG. 2.

Referring now to FIGS. 2 and 3, an embodiment of a method of automated fluid pressure control is presented. The syringe size is input 70 and either a full stroke delivery or a measured volume delivery is selected 72. The desired administration pressure $P_{input}$, the delivery volume $V_{input}$, and the maximum time of inflation $T_{input}$ are entered 74, although a default time value such as ninety seconds may be used. The processor 66 converts 76 the delivery pressure $P_{input}$ to the pressure to be provided by the regulator 52 $P_{reg}$. The processor 66 also converts 78 the delivery volume $V_{input}$ to plunger travel distance $d_{input}$ according to the syringe size. Next, the air cylinder 50 is vented 80, the solenoid activated 82 and the syringe and slide mechanism 48 are manually aligned 84 with the syringe plunger 38 being engaged. The delivery sequence is initiated 86 and the starting voltage from the linear resistor 58 is read 88 as the zero travel distance. The timer is started 90 and the pressure $P_{reg}$ to be maintained by the regulator 52 is sent to the regulator. The travel distance "d" of the slide mechanism 48 and the time "t" are continually monitored 94 and 96 and when either $d = d_{input}$ or $t = t_{input}$, the timer is stopped 98 and the cylinder retracted 100 for removal or further disposition of the catheter 42.

In an alternate embodiment, the volume of fluid to be administered may be entered by means of a cassette identifier. Entry of the cassette identifier will inform the processor 66 of the end-of-travel position for that particular cassette and may also include the maximum pressure $P_{max}$ permitted with that cassette. This information may be provided by means of a bar code placed on the cassette which may be read by a bar code reader (not shown) attached to the processor 66. Use of the term "cassette" is not meant to be limiting. The cassette referred to may take the form of a syringe or other device which performs the function of a fluid reservoir. A look-up table containing information corresponding to each of the possible cassettes usable in the system may be included with the processor 66.

Figure 4:
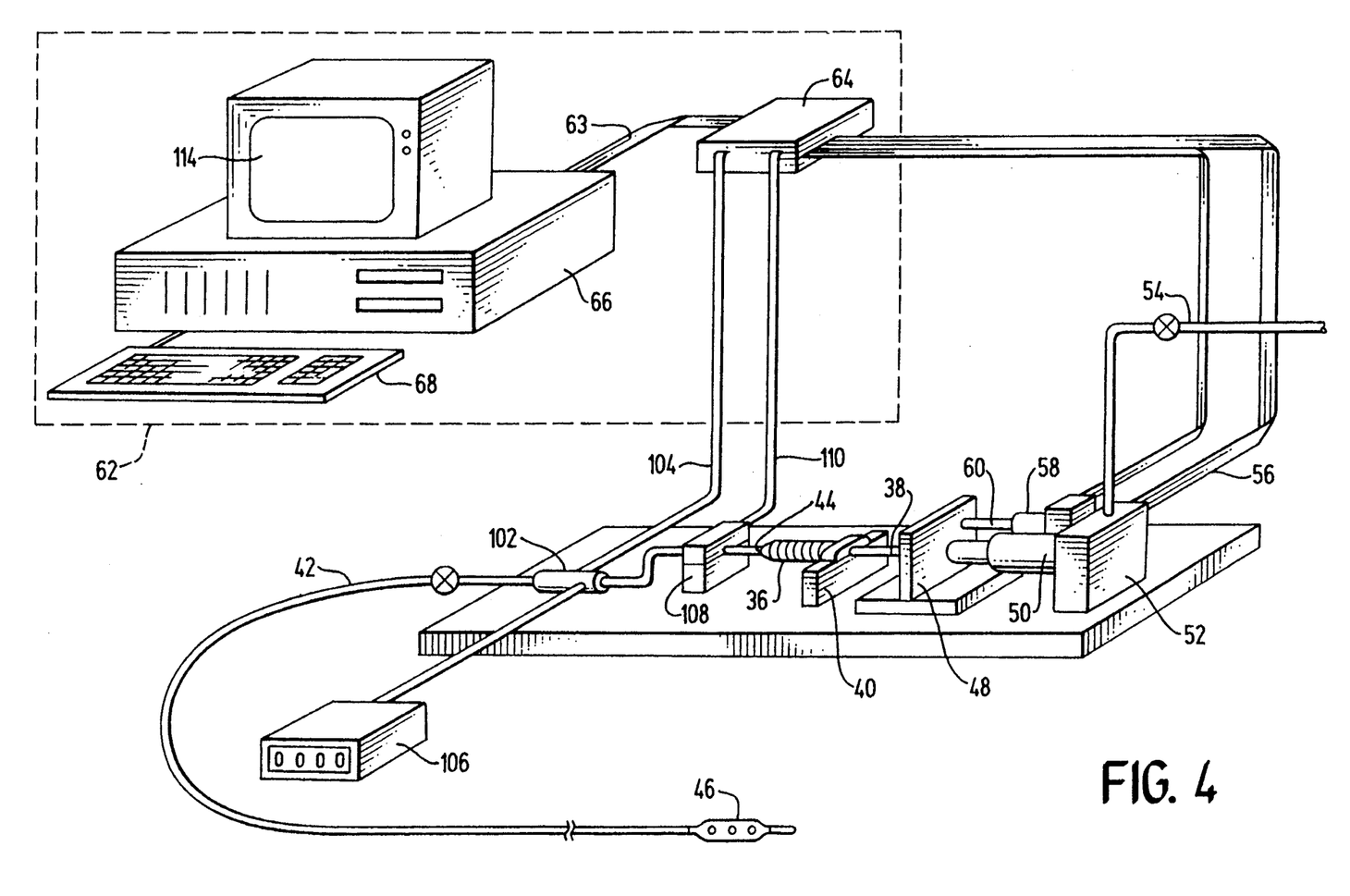
FIG. 4 is a schematic/block diagram of an automated fluid pressure control system supplying a medical fluid to an inflation balloon using a pneumatic driver, a syringe as the fluid reservoir, an air-in-line detector, a pressure detector in the catheter line, and a volume detector.

Referring now to FIG. 4, a second embodiment of an automated fluid pressure control system is presented. As in FIG. 2, a fluid reservoir comprising a syringe 36 and a pneumatic driver for moving the syringe plunger 38 are used to control the pressure of the fluid in the syringe 36. The fluid is forced out of the syringe 36, into the catheter 42 and into the delivery device which, in this case, is an inflatable balloon 46. However, the system of FIG. 4 also includes a pressure sensor 102 for monitoring the pressure of the fluid. The pressure sensor 102 may take the form of a silicon piezo-resistor which is responsive to pressure within the fluid between the output port 44 of the syringe 36 and the catheter 42. A commonly available pressure sensor is the MPX-700D from Motorola. The pressure sensed is provided to the interface unit 64 on line 104 for conversion to a digital signal and for forwarding to the processor 66. Additionally, a pressure display 106 is provided for monitoring the pressure of the fluid being delivered.

The processor 66 compares the digital pressure signal to the desired administration pressure and outputs on the bus 63 an error signal. The interface unit 64 converts that digital error signal to an analog signal for forwarding to the air pressure controller 52. However, in the embodiment where a pressure regulator is used such as the QB electro-pneumatic regulator which converts the input signal to a pressure, the error signal must be added to or subtracted from the desired pressure signal provided to the regulator. In this embodiment, there are two pressure controls. The pressure regulator 52 itself monitors its own output while the additional pressure sensor 102 mounted at the output of the syringe 36 also monitors pressure.

A further feature incorporated in the system of FIG. 4 is an air-in-line sensor 108 for detecting air bubbles. The output of the air-in-line sensor is transmitted on line 110 to the interface unit 64 for conversion to a digital signal and is then transmitted to the processor 66. In the event that an air bubble of a particular size is detected, the processor 66 may stop delivery of the fluid by the pneumatic driver and provide an alarm. Such air-in-line sensors are available from Zevex, Inc. in Murray, Utah. Alarms, such as those for air-in-line and pressure, may be provided by a display 114 connected to the processor 66 and may also be given audibly.

Known techniques for increasing the accuracy of the volume detection of fluid delivered to the delivery device 46 may be employed. For example, slope, offset and scale factors may be stored and made available to the processor 66 for each displacement detector 58 used. Different syringes or cassettes may be used with the system, each of which has a look-up table made available to the processor 66. Techniques other than look-up tables may be used such as interpolation between beginning-of-travel and end-of-travel points. The operator may be prompted for a cassette code and upon entering that code, the processor may then create a look-up table for that cassette based on characteristic data of the cassette previously stored.

Processing techniques for smoothing pneumatic driver 50 and 52 responses may be included in the processor 66. For example, a classical proportional, integral, derivative control system may be used.

Figure 5A:
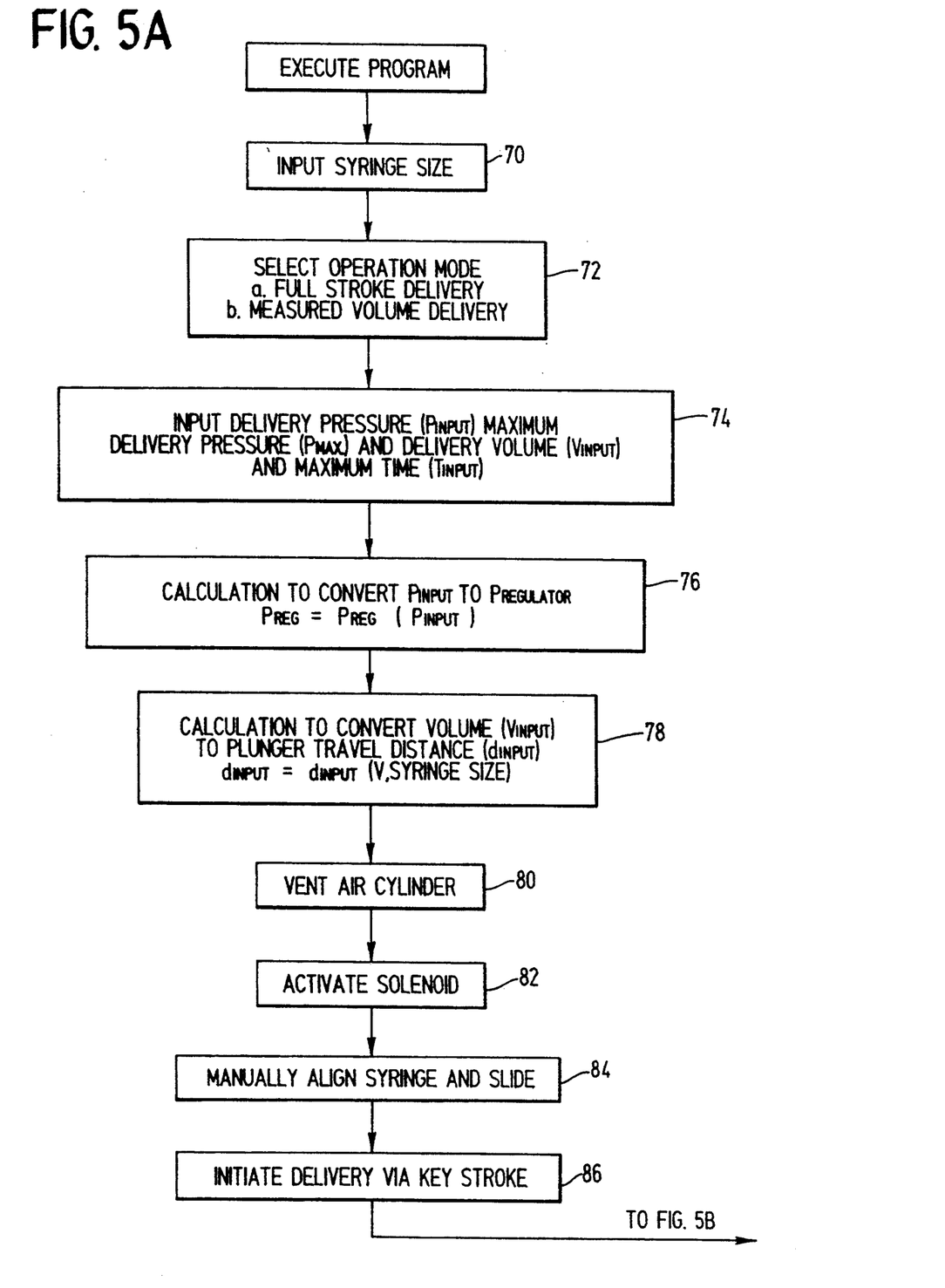
FIG. 5A and 5B is a flow chart presenting a method of automated fluid pressure control in an automated fluid pressure control system such as that shown in FIG. 4.
Figure 5B:
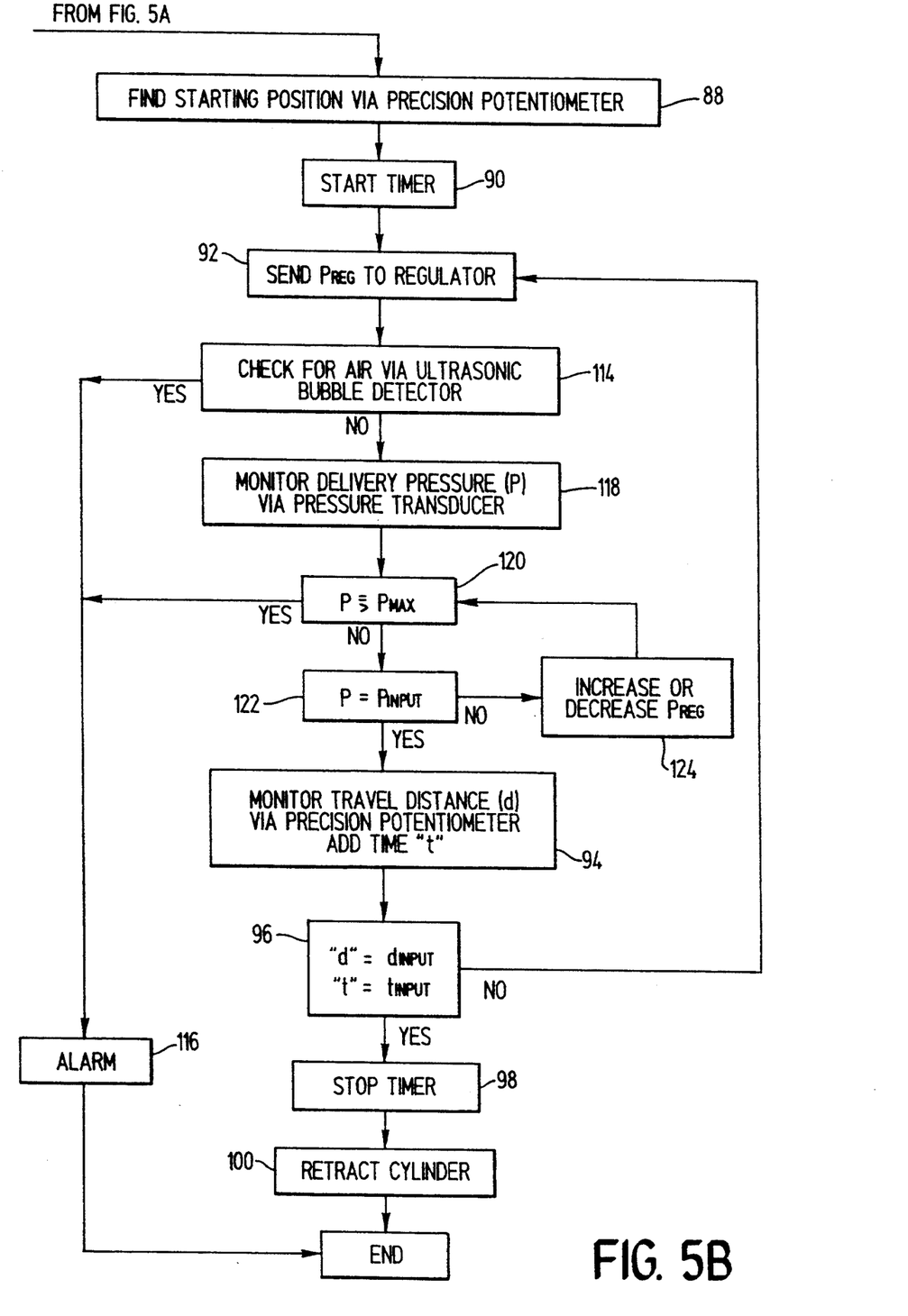

Referring now to FIG. 4 and FIGS. 5A and 5B, an embodiment of a method for automated fluid pressure control is presented. The syringe size is input 70 and either a full stroke delivery or a measured volume delivery is selected 72. The desired administration pressure $P_{input}$, the maximum pressure $P_{max}$, the delivery volume $V_{input}$, and the maximum time of inflation $T_{input}$ are entered 74, although a default time value such as ninety seconds may be used. The processor 66 converts 76 the delivery pressure $P_{input}$ to the pressure to be provided by the regulator 52 $P_{reg}$. The processor 66 also converts 78 the delivery volume $V_{input}$, to plunger travel distance $d_{input}$ according to the syringe size. Next, the air cylinder 50 is vented 80, the solenoid activated 82 and the syringe and slide mechanism 48 are manually aligned 84 with the syringe plunger 38 being engaged. The delivery sequence is initiated 86 and the starting voltage from the linear resistor 58 is read 88 as the zero travel distance. The timer is started 90 and the pressure $P_{reg}$ to be maintained by the regulator 52 is sent to the regulator at 92. In other embodiments, the timer may be automatically started upon reaching a predetermined minimum pressure, as measured by the pressure sensor 102; for example, two atmospheres.

The fluid line is monitored 114 for the existence of air and if an unacceptably high amount of air is detected, an alarm is provided 116. The delivery pressure is continuously monitored 118 and if that pressure equals or exceeds $P_{max}$ 120, an alarm is provided 116. If the delivery pressure is not equal to $P_{input}$ 122, the delivery pressure is increased or decreased 124 until $P_{input}$ is reached. The travel distance of the slide mechanism 48 is continually monitored 94 and 96 and when either the distance traveled "d" equals $d_{input}$ or the time expired "t" equals $t_{input}$, the timer is stopped 98 and the cylinder retracted 100 for removal or further disposition of the catheter 42.

An end-of-travel determination of the syringe plunger may be made in the above embodiments. In one technique, the end of travel displacement may be programmed into the processor 66 as a characteristic of each cassette used. This data may reside in a look-up table in the processor or be input to the processor 66 in other ways. In another technique, the displacement sensor may be monitored for change and in the event that no further change occurs, the end of travel of the syringe plunger may be assumed. In the case of FIGS. 3 and 5 where step 72 requires a selection of full stroke delivery or measured volume delivery, the full stroke delivery may be determined by end of travel.

Additionally, a higher initial pressure may be programmed into the processor 66 for starting the fluid delivery. This initial pressure would be greater than $P_{input}$ and would cause rapid inflation of the delivery device so that a minimum loss of inflation fluid occurs.

After inflating, the pressure would then be reduced to $P_{input}$.

A pneumatic power source typically available in most hospital rooms is the 100 psi air provided at a wall fitting. A connecting hose 54 may be coupled between the wall fitting and the air pressure controller 52 to provide a pneumatic energy source for the air cylinder 50. The use of pneumatic power rather than electrical power to pressurize the delivery fluid reduces the electrical hazard to the patient.

It was found that a pneumatic system provided the needed ramp-up speed to quickly inflate the balloon with the fluid to be administered while allowing losing only an insignificant amount of the fluid to enter the bloodstream during inflation. Other driver systems may be used, such as a motor system using a stepper motor. However, it was also found that a pneumatic system offered a cost effective system which may be contained in a relatively small and light weight case. Pneumatic energy is readily available in most hospital rooms; hence, no portable source of power, such as an air cylinder, need be included in one embodiment. In another embodiment where air pressure is not available from the room, a portable air cylinder may be used. The embodiment using pneumatic power provides a rapid response and accurate control. In the case where a stepper motor is used to provide the driving means, a more complex, heavier and more expensive system may result because of the addition of the stepper motor itself.

Additionally, the driver 18 may take forms other than a volume controller of the reservoir 14. A device which draws the fluid from the reservoir without varying the volume of the reservoir may be used.

The systems and methods described above may be used with an angioplasty catheter to accurately control the pressure of the inflated balloon, although the air-in-line sensor 108 and the displacement detector 58 would have limited value. Additionally, the systems and methods of the FIGS. are not limited to applications involving only the blood vessels. They may be used in procedures with organs such as the kidney, the liver; and used in other procedures such as with the prostate and in other ducts.

Although specific embodiments of the invention have been described and illustrated, it is clear that the invention is susceptible to numerous modifications and embodiments within the ability of those skilled in the art, and without the exercise of the inventive faculty. Thus, it should be understood that various changes in form, detail and application of the present invention may be made without departing from the spirit and scope of the invention.

What is claimed is:

1. An apparatus for providing fluid at a predetermined pressure to the walls of a delivery site internal to the body of a patient, the apparatus comprising:

an inflatable delivery device which when inflated, contacts the walls of the delivery site, the delivery device having at least one aperture which is positioned in contact with the wall of the delivery site when the delivery device is inflated and through which the fluid will flow into the wall;

a reservoir containing the fluid;

a conduit connected between the reservoir and the delivery device to conduct the fluid therebetween;

driving means for varying the pressure of the fluid;

a pressure sensor means for automatically sensing the pressure of said fluid and for providing a sensed pressure signal representative of the sensed pressure;

a volume detector which detects the volume of the fluid delivered and provides a volume signal representative of the detected volume delivered; and a controller which automatically receives the sensed pressure signal, automatically compares the sensed pressure signal to a target pressure signal representative of the predetermined pressure, automatically provides a pressure error signal representative of the difference between the sensed pressure signal and the target pressure signal, and automatically controls the driving means to vary the pressure of the fluid in accordance with the error signal to attain the predetermined pressure;

wherein the controller compares the volume signal to a target volume signal representative of a predetermined volume of fluid to be delivered and controls the pneumatic driver to cease delivery of the fluid when the volume signal and the target volume signal are equal.

2. The apparatus of claim 1 wherein the driving means comprises:

a driving member which varies the volume of the reservoir to thereby control the pressure of the fluid;

a pneumatic driver which moves the driving member in response to pneumatic pressure; and wherein the controller controls the pneumatic driver to move the driving member in accordance with the error signal to attain the predetermined pressure.

3. The apparatus of claim 1 wherein:

the controller provides an alarm in the event that the sensed pressure signal indicates a pressure below a predetermined threshold pressure while the volume signal indicates that fluid continues to be delivered.

4. The apparatus of claim 1 wherein the reservoir comprises a syringe having a barrel containing the fluid, the barrel having an output port to which the conduit is connected and a plunger which is movable to vary the volume of fluid in the barrel; and wherein the driving means is for moving the plunger in relation to the barrel to control the pressure in accordance with the error signal.

5. The apparatus of claim 1 wherein the controller times the sensed pressure signal for the amount of time the sensed pressure exceeds a predetermined threshold and upon reaching a predetermined time limit, controls the driving means to cease delivery of the fluid.

6. An apparatus for providing a predetermined amount of fluid at a predetermined pressure to a delivery device positioned at a delivery site internal to the body of a patient, the apparatus comprising:

a conduit adapted to be connected to the delivery device;

a reservoir containing the fluid wherein the reservoir comprises a syringe having a barrel containing the fluid, the barrel having an output port to which the conduit is connected and a plunger which is movable to vary the volume of fluid in the barrel;

a pneumatic driver which moves the plunger in relation to the barrel to control the fluid pressure in response to pneumatic pressure;

a pressure sensor means for automatically sensing the pressure of the fluid and for providing a sensed pressure signal representative of the sensed pressure;

a controller which automatically receives the sensed pressure signal, automatically compares the sensed pressure signal to a target pressure signal representative of the predetermined pressure, automatically provides a pressure error signal representative of the difference between the sensed pressure signal and the target pressure signal, and automatically controls the pneumatic driver to move the plunger in accordance with the error signal to attain the predetermined pressure;

a volume detector which detects the volume of the fluid delivered by the syringe and provides a volume signal representative of the detected volume delivered; and the controller further automatically compares the volume signal to a target volume signal representative of the predetermined volume of fluid to be delivered and controls the pneumatic driver to cease delivery of the fluid when the volume signal and the target volume signal are equal.

7. The apparatus of claim 6 wherein the volume detector comprises a linear resistor oriented along the path of travel of the driver and coupled for detecting the position of the driver, the resistor providing a position signal corresponding to the position of the plunger wherein the volume signal comprises the position signal; and wherein the controller receives the position signal, compares the position signal to a target position signal representative of a predetermined position corresponding to the predetermined volume, and controls the pneumatic driver to cease delivery of the fluid when the position signal and the target position signal are equal.

8. The apparatus of claim 6 wherein the controller compares the volume signal to an end-of-travel signal representative of the end of the travel of the driver and upon the volume signal equalling the end-of-travel signal, provides an end-of-travel alarm.

9. An apparatus for administering a predetermined volume of fluid to a delivery site internal to the body of a patient at a predetermined pressure through a delivery device having a aperture, the apparatus comprising:

a reservoir containing the fluid;

a conduit adapted to be connected between the reservoir and the delivery device;

a pneumatic driver;

a driving member operated upon by the pneumatic driver for varying the pressure of the fluid and causing the fluid to flow from the reservoir to the delivery device;

a pressure sensor means for sensing the pressure of the fluid and for providing a sensed pressure signal representative thereof;

a volume detector which detects the volume of the medical fluid provided from the reservoir through the conduit and which provides a volume signal representative of the detected volume provided;

a controller which automatically receives the sensed pressure signal, automatically compares the sensed pressure signal to a target pressure signal representative of the predetermined pressure, automatically provides a pressure error signal representative of the difference between the sensed pressure signal and the target pressure signal and automatically controls the pneumatic driver to vary the pressure of the fluid in accordance with the error signal to attain the predetermined pressure, the controller also automatically comparing the volume signal to a target volume signal representative of the predetermined volume of fluid to be delivered and automatically controlling the driving means to cease delivery of the fluid when the volume signal equals the target fluid signal.

10. The apparatus of claim 9 wherein the reservoir comprises a syringe having a barrel containing the fluid, the barrel having an output port to which the conduit is connected and a plunger which is movable to vary the volume of fluid in the barrel; and wherein the driving member moves the plunger in relation to the barrel to vary the volume of the reservoir to thereby control the pressure of the fluid in accordance with the error signal.

11. The apparatus of claim 10 wherein the volume detector comprises a displacement detector which monitors the movement of the syringe plunger to determine the volume applied and provides a position signal corresponding to the position of the plunger, wherein the volume signal comprises the position signal; and wherein the controller receives the position signal, compares the position signal to a target position signal representative of a predetermined position corresponding to a predetermined volume of the fluid to be delivered, and controls the driving means to cease delivery of the fluid when the position signal and the target position signal are equal.

12. The apparatus of claim 11 wherein the displacement detector comprises a linear resistor oriented along the path of travel of the driving member and coupled for detecting the position of the driving member, the resistor providing the position signal corresponding to the position of the plunger.

13. The apparatus of claim 9 wherein the controller provides an alarm in the event that the sensed pressure signal indicates a pressure below a predetermined threshold pressure while the volume signal indicates that fluid continues to be delivered.

14. A method for administering a predetermined volume of fluid at a predetermined pressure to a delivery device positioned at a delivery site internal to the body of a patient, the method comprising the steps of:

containing the fluid to be delivered in a reservoir comprising a syringe having a barrel and a plunger movable in the barrel for controlling the movement of the fluid into and out of the barrel;

controlling the fluid pressure by moving the plunger with a pneumatic driver in relation to the barrel in response to pneumatic pressure to move the fluid from the reservoir through a fluid conduit and to the delivery device;

sensing the pressure of the fluid and providing a sensed pressure signal representative of the sensed pressure;

automatically comparing the sensed pressure to the predetermined pressure;

automatically varying the application of pneumatic pressure in accordance with the pressure difference between the sensed pressure and the predetermined pressure to attain the predetermined pressure;

sensing the volume of the fluid delivered and providing a volume signal representative of the detected volume delivered; and comparing the volume signal to a target volume signal representative of a predetermined volume of fluid to be delivered and controlling the pneumatic driver to cease delivery of the fluid when the volume signal and the target volume signal are equal.

15. The method of claim 14 further comprising the steps of comparing the volume signal to an end-of-travel signal representative of the end of travel of the pneumatic driver and upon the volume signal equalling the end-of-travel signal, providing an end-of-travel alarm.

16. The method of claim 14 further comprising the steps of:
comparing the sensed pressure to a predetermined threshold pressure;
monitoring fluid volume delivered; and
providing an alarm in the event that the sensed pressure is below the predetermined threshold pressure while the volume of fluid delivered continues to increase.

17. The method of claim 15 wherein:
the step of containing the fluid in a reservoir comprises the step of containing the fluid in the barrel of a syringe and comprises the further step of connecting the conduit to the output port of the syringe.

18. A method for providing fluid at a predetermined pressure to the walls of a delivery site internal to the body of a patient, the method comprising the steps of:
positioning an inflatable delivery device in contact with the walls of the delivery site, the delivery device having at least one aperture which is positioned in contact with a wall of the delivery site through which the fluid will flow into the wall;
containing the fluid in a reservoir;
connecting a conduit between the reservoir and the delivery device to conduct the fluid therebetween;
controlling the fluid pressure by applying pneumatic pressure to cause the reservoir to expel the fluid at a greater and lesser rate;
automatically sensing the pressure of the fluid and providing a sensed pressure signal representative of the sensed pressure;
detecting the volume of the fluid delivered from the reservoir and providing a volume signal representative of the detected volume delivered;
automatically comparing the sensed pressure signal to a target pressure signal representative of the predetermined pressure;
automatically providing a pressure error signal representative of the difference between the sensed pressure signal and the target pressure signal to automatically control the pneumatic pressure to vary the pressure of the fluid in accordance with the error signal to attain the predetermined pressure;
automatically comparing the volume signal to a target volume signal representative of a predetermined volume of fluid to be delivered; and
controlling the pneumatic pressure to cease delivery of the fluid when the volume signal and the target volume signal are equal.

19. The method of claim 21 wherein:
the step of controlling the fluid pressure varying the volume of the reservoir by means of a pneumatic driver in response to the pneumatic pressure to thereby control the pressure of the fluid.

20. The method of claim 19 further comprising the steps of comparing the volume signal to an end-of-travel signal representative of the end of travel of the pneumatic driver and upon the volume signal equalling the end-of-travel signal, providing an end-of-travel alarm.

21. The method of claim 20 further comprising the steps of:
comparing the sensed pressure to a predetermined threshold pressure;
monitoring fluid volume delivered; and
providing an alarm in the event that the sensed pressure is below the predetermined threshold pressure while the volume of fluid delivered continues to increase.

* * * * *

UNITED STATES PATENT AND TRADEMARK OFFICE
CERTIFICATE OF CORRECTION

PATENT NO. : 5,342,298

DATED : August 30, 1994

INVENTOR(S) : Mary. B. Michaels, Janine C. Robinson, John P. Claude, Donald L. Alden It is certified that error appears in the above-identified patent and that said Letters Patent is hereby corrected as shown below:

Claim 19, column 16, line 22, change "21" to --18--.

Signed and Sealed this

Fifth Day of March, 1996

Attest:

BRUCE LEHMAN

*Attesting Officer*     *Commissioner of Patents and Trademarks*